(12) United States Patent
Robinson et al.

(10) Patent No.: US 9,376,372 B2
(45) Date of Patent: Jun. 28, 2016

(54) PROCESS FOR PRODUCING AMINE COMPOUNDS

(71) Applicant: Monash University, Victoria (AU)

(72) Inventors: Andrea J Robinson, Victoria (AU); Nicolas Spiccia, Victoria (AU); William Roy Jackson, Victoria (AU); Clint Woodward, Victoria (AU)

(73) Assignee: Monash University, Victoria (AU)

( * ) Notice: Subject to any disclaimer, the term of this patent is extended or adjusted under 35 U.S.C. 154(b) by 0 days.

(21) Appl. No.: 14/412,633

(22) PCT Filed: Jul. 8, 2013

(86) PCT No.: PCT/AU2013/000745
§ 371 (c)(1),
(2) Date: Jan. 2, 2015

(87) PCT Pub. No.: WO2014/005196
PCT Pub. Date: Jan. 9, 2014

(65) Prior Publication Data
US 2015/0183724 A1    Jul. 2, 2015

(30) Foreign Application Priority Data
Jul. 6, 2012   (AU) ................................ 2012902915

(51) Int. Cl.
*C07C 227/16* (2006.01)
*C07C 209/68* (2006.01)
*C07C 209/70* (2006.01)
*C07D 213/127* (2006.01)
*C07B 37/08* (2006.01)
*C07B 35/02* (2006.01)

(52) U.S. Cl.
CPC .............. *C07C 227/16* (2013.01); *C07B 35/02* (2013.01); *C07B 37/08* (2013.01); *C07C 209/68* (2013.01); *C07C 209/70* (2013.01); *C07D 213/127* (2013.01)

(58) Field of Classification Search
CPC .. C07C 227/16; C07C 209/70; C07C 209/68; C07B 35/02
See application file for complete search history.

(56) References Cited

U.S. PATENT DOCUMENTS

2013/0116458 A1* 5/2013 Couturier et al. .............. 554/114

FOREIGN PATENT DOCUMENTS

| WO | 2005068643 A2 | 7/2005 |
| WO | 2011078667 A2 | 6/2011 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Chatterjee et al, Journal of the American Chemical Society, A General Model for Selectivity in Olefin Cross Metathesis, 2003, 125, pp. 11360-11370.*
Vedrenne et al, Synlett, Dramatic Effect of Boron-Based Lewis Acids in Cross-Metathesis Reactions, 2005, 4, pp. 670-672.*
Woodward, C.P. et al, 'A Simple Amine Protection Strategy for Olefin Metathesis Reactions', Chem. Commun., 2011, vol. 47, pp. 779-781.
Connon, S.J. et al, 'A Solid-Supported Phosphine-Free Ruthenium Alkylidene for Olefin Metathesis in Methanol and Water', Bioorg. Med. Chem. Lett., 2002, vol. 12, pp. 1873-1876.
Alcaide, B. et al, 'Grubbs' Ruthenium-Carbenes Beyond the Metathesis Reaction: Less Conventional Non-Metathetic Utility', Chem. Rev., 2009, vol. 109, pp. 3817-3858. S.
Gulajski, L. et al, 'A Highly Active Aqueous Olefin Metathesis Catalyst Bearing a Quaternary Ammonium Group', ChemSusChem, 2008, vol. 1, pp. 103-109.
Abbas et al., "Optimized reaction conditions for the cross-metathesis of methyl oleate and oleylamine with ethyl acrylate," Monatsh Chem, 2012, 143:669-673.
Bowers et al., "Synthesis and Conformation—Activity Relationships of the Peptide Isosteres of FK228 and Largazole," Am. Chem. Soc., Feb. 4, 2009, 131:2900-2905.
European Patent Office, Extended European Search Reort for PCT/AU2013000745 dated Jan. 19, 2016.

* cited by examiner

*Primary Examiner* — Paul A Zucker
(74) *Attorney, Agent, or Firm* — Tracey S. Truitt; Polsinelli PC

(57) ABSTRACT

The present invention provides processes for producing amine compounds. The amine compounds include diammonium compounds and amino acid derivatives.

13 Claims, No Drawings

US 9,376,372 B2

PROCESS FOR PRODUCING AMINE COMPOUNDS

FIELD OF THE INVENTION

The invention relates to processes for producing amine compounds. The amine compounds include diammonium compounds and amino acid derivatives.

BACKGROUND OF THE INVENTION

Amine compounds have many applications in industry, particularly in the synthesis of polymers such as polyamides and polyamines. Amine compounds also have specialty applications as boutique monomers in a number of polymer applications.

Industrial processes that are currently used to produce many amine compounds have an adverse environmental impact. For example, the synthesis of 1,6-diaminohexane involves the use of adiponitrile, which is a carcinogen. Similarly, production of the monomer caprolactam produces 5 kg of ammonium sulfate for every 1 kg of monomer produced. The synthesis of 1,6-diaminohexane and caprolactam are of particular concern, as these monomers are used to produce Nylon66 and Nylon6 respectively, which constitute approximately 90% of the world's overall polyamide usage and 99% of polyamide fibers.

It would therefore be desirable to provide processes for preparing amine compounds of these types that rely on greener technologies than those currently used in industry.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

STATEMENT OF INVENTION

The present invention provides processes for producing amine compounds. The amine compounds include diammonium compounds and amino acid derivatives.

One aspect of the present invention is to provide a process for producing a diammonium salt comprising the steps of providing an unsaturated amine salt and subjecting the unsaturated amine salt to self-metathesis in the presence of a metathesis catalyst to give a diammonium salt.

In one embodiment, the unsaturated amine salt is a compound of Formula I

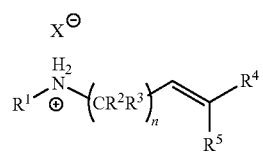

Formula I wherein
each $R^1$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

each $R^2$ and $R^3$ are each independently selected from the group consisting of H, optionally substituted $C_1$-$C_{12}$alkyl, $C(=O)R^6$, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

$R^4$ and $R^5$ are each independently selected from the group consisting of H, optionally substituted $C_1$-$C_{20}$alkyl, $(CR^2R^3)_nNH_2^+R^1$, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

each n is an integer independently selected from the group consisting of 1, 2, 3, 4, 5, 6, 7, 8, 9, 10, 11, 12, 13, 14, 15, 16, 17, 18, 19 and 20;

$X^-$ is a counterion;

$R^6$ is $NR^{6a}R^{6b}$; and $R^{6a}$ and $R^{6b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino.

In one embodiment, $R^1$ is H. In another embodiment, $R^2$ is H. In still another embodiment, $R^3$ is H. In a further embodiment, n is an integer selected from the group consisting of 1, 2 and 3. In still a further embodiment, $R^4$ is H. In yet a further embodiment, $R^5$ is H.

In one embodiment, the counterion $X^-$ is selected from the group consisting of $BF_4^-$, $TsO^-$, $Cl^-$, $TfO^-$, $TFA^-$, $Adipate^{2-}$, $BSA^-$, $MsO^-$, $HSO_4^-$, $F^-$, $Br^-$, $I^-$, $H_2AsO_4^-$, $H_2PO_4^-$, $H_2AsO_3^-$, $HPO_4^{2-}$, $H_2PO_4^-$, $SO_4^{2-}$, $NO_3^-$, $NO_2^-$, $S_2O_3^{2-}$, $HSO_3^-$, $ClO_4^-$, $IO_3^-$, $ClO_3^-$, $BrO_3^-$, $ClO_2^-$, $CrO_4^{2-}$, $HCO_3^-$, $Cr_2O_7^{2-}$, $ClCH_2COO^-$, $HCOO^-$, $OCN^-$, $HC_2O_4^-$, $B(OR)_4^-$, $B(OH)_4^-$, $CF_2HSO_2$—$O^-$, $CFH_2SO_2$—$O^-$ and alkyl aryl sulfonates. In a further embodiment $X^-$ is selected from the group consisting of $BF_4^-$, $TsO^-$ and $TfO^-$.

In one embodiment, the metathesis catalyst is a Hoveyda Grubbs second generation catalyst. The self-metathesis step may be performed in a solvent in which the unsaturated amine salt is more soluble than the diammonium salt. In one embodiment the solvent is selected from the group consisting of $CH_2Cl_2$, EtOAc and mixtures thereof. In one embodiment, the self-metathesis step is performed at a temperature ranging from 0 degrees Celsius to 100 degrees Celsius. In another embodiment the self-metathesis step is performed under microwave irradiation.

The process for producing a diammonium salt may further comprise a step of hydrogenating the diammonium salt formed from self-metathesis to give a saturated diammonium salt. In one embodiment, the self-metathesis step and the hydrogenating step are performed in series, without isolation of the diammonium salt after self-metathesis. A further solvent may be added after the self-metathesis step and prior to the hydrogenating step. In one embodiment the further solvent is a protic solvent, such as methanol.

The hydrogenating step may be performed in the presence of hydrogen gas. In one embodiment, the hydrogenating step is performed at a hydrogen pressure of 0 to 90 psi $H_2$. In a further embodiment the hydrogen pressure is 60 psi. The hydrogenating step may be performed at a temperature ranging from 0 degrees Celsius to 100 degrees Celsius. In one embodiment the hydrogenating step is performed at standard laboratory conditions.

Another aspect of the present invention is to provide a process for producing an amino acid salt or derivative thereof comprising the steps of providing an unsaturated amine salt or derivative thereof and subjecting the unsaturated amine salt or derivative thereof to cross-metathesis with a compound of Formula II

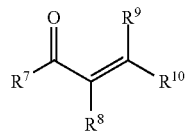

Formula II wherein $R^7$ is selected from the group consisting of OH, $OR^{7a}$ and $NR^{7a}R^{7b}$;

$R^8$ is selected from the group consisting of H and $C_1$-$C_{12}$alkyl;

$R^9$ and $R^{10}$ are each independently selected from the group consisting of H, $C_1$-$C_{12}$alkyl, $C_2$-$C_{12}$alkenyl, $C_2$-$C_{12}$alkynyl and C(=O)$R^7$; and $R^{7a}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

in the presence of a metathesis catalyst to give the amino acid salt or derivative thereof.

In one embodiment, $R^7$ is OH. In another embodiment, $R^7$ is $OC_1$-$C_6$ alkyl. In still another embodiment, $R^7$ is $OC_4$alkyl. In a further embodiment $R^8$ is H. In still a further embodiment $R^9$ is H. In another embodiment, $R^{10}$ is H. In one embodiment, the compound of Formula II is a compound of Formula III

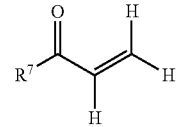

Formula III wherein $R^7$ is selected from the group consisting of OH, $OR^{7a}$ and $NR^{7a}R^{7b}$; and $R^{7a}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino.

In one embodiment, the unsaturated amine salt or derivative thereof is a compound of Formula I as previously described.

In one embodiment, the metathesis catalyst is a Hoveyda Grubbs second generation catalyst. The cross-metathesis step may be performed in a solvent in which the unsaturated amine salt is more soluble than the amino acid salt. In one embodiment the solvent is selected from the group consisting of $CH_2Cl_2$, EtOAc and mixtures thereof. In another embodiment the solvent is EtOAc. In one embodiment, the cross-metathesis step is performed at a temperature ranging from 0 degrees Celsius to 100 degrees Celsius. In another embodiment the cross-metathesis step is performed under microwave irradiation.

The process for producing an amino acid salt or derivative thereof may further comprise a step of hydrogenating the amino acid salt or derivative thereof formed from cross-metathesis to give a saturated amino acid salt or derivative thereof. In one embodiment, the cross-metathesis step and the hydrogenating step are performed in series, without isolation of the amino acid salt or derivative thereof after cross-metathesis. A further solvent may be added after the cross-metathesis step and prior to the hydrogenating step. In one embodiment the further solvent is a protic solvent, such as methanol.

The hydrogenating step may be performed in the presence of hydrogen gas. In one embodiment, the hydrogenating step is performed at a hydrogen pressure of 0 to 200 psi $H_2$. In a further embodiment the hydrogen pressure is 90 psi. The hydrogenating step may be performed at a temperature ranging from 0 degrees Celsius to 100 degrees Celsius. In one embodiment the hydrogenating step is performed at 60 degrees Celsius.

DETAILED DESCRIPTION OF THE INVENTION

In this specification a number of terms are used which are well known to a skilled addressee. Nevertheless for the purposes of clarity a number of terms will be defined.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, heteroalkyl, cycloalkyl, cycloalkenyl, heterocycloalkyl, heterocycloalkenyl, aryl, heteroaryl, hydroxy, alkyloxy, alkenyloxy, alkynyloxy, cycloalkyloxy, cycloalkenyloxy, heterocycloalkyloxy, heterocycloalkenyloxy, aryloxy, heteroaryloxy, arylalkyloxy, amino, alkylamino, —C(=O)OH, —C(=O)$R^e$, —C(=O)$OR^e$, C(=O)$NR^eR^f$, C(=NOH)$R^e$, C(=$NR^e$)$NR^fR^g$, $NR^eR^f$, $NR^eC(=O)R^f$, $NR^eC(=O)OR^f$, $NR^eC(=O)NR^fR^g$, $NR^eC(=NR^f)$$NR^gR^h$, $NR^eSO_2R^f$, —$SR^e$, $SO_2NR^eR^f$, —$OR^e$, OC(=O)$NR^eR^f$, OC(=O)$R^e$ and acyl, wherein $R^e$, $R^f$, $R^g$ and $R^h$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_1$-$C_{10}$heteroalkyl, $C_3$-$C_{12}$cycloalkyl, $C_3$-$C_{12}$cycloalkenyl, $C_1$-$C_{12}$heterocycloalkyl, $C_1$-$C_{12}$heterocycloalkenyl, $C_6$-$C_{18}$aryl, $C_1$-$C_{18}$heteroaryl, and acyl, or any two or more of $R^e$, $R^f$, $R^g$ and $R^h$, when taken together with the atoms to which they are attached form a heterocyclic ring system with 3 to 12 ring atoms.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are $C_1$-$C_6$alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a $C_1$-$C_{12}$alkyl, more preferably a $C_1$-$C_{10}$alkyl, most preferably $C_1$-$C_6$ unless otherwise noted. Examples of suitable straight and branched $C_1$-$C_6$alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means an Alkyl-NH— group, in which alkyl is as defined herein. "Dialkylamino" means a (alkyl)$_2$N— group, in which each alkyl may be the same or different and are each as defined herein for alkyl. The alkyl group is preferably a $C_1$-$C_6$alkyl group. The group may be a terminal group or a bridging group. If the group is a terminal group it is bonded to the remainder of the molecule through the nitrogen atom.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group it is bonded to the remainder of the molecule through the oxygen atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_5$-$C_7$cycloalkyl or $C_{5-7}$cycloalkenyl group are fused together to form a cyclic structure, such as tetrahydronaphthyl, indenyl or indanyl. The group may be a terminal group or a bridging group. Typically an aryl group is a $C_6$-$C_{18}$aryl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$alkyl group. The group may be a terminal group or a bridging group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

As used herein the term "derivative thereof" refers to a direct derivative of the referenced species and with particular reference to amino acids includes esters and amides of the amino acid.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$ alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to a heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$heteroaryl group. The group may be a terminal group or a bridging group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocycloalkenyl" refers to a heterocycloalkyl group as defined herein but containing at least one double bond. A heterocycloalkenyl group typically is a $C_2$-$C_{12}$heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$heterocycloalkyl group. The group may be a terminal group or a bridging group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$Heterocycloalkenyloxy. The group may be a terminal group or a bridging group. If the group is a terminal group it is bonded to the remainder of the molecule through the oxygen atom.

"Protic" refers to any solvent that contains a dissociable H+ (proton).

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula I, Formula II and Formula III are intended to cover, where applicable, solvated as well as unsolvated forms of the compounds. Thus, each formula includes compounds having the indicated structure, including the hydrated as well as the non-hydrated forms.

As used throughout the specification a suitable solvent is a solvent or solvent mixture that does not interfere with the designated reaction. Suitable solvents are known in the art for most reactions and will be selected depending upon the reaction conditions.

Processes for Producing Amine Compounds

As stated previously, an aspect of the present invention is to provide processes for producing amine compounds. The amine compounds include diammonium compounds and amino acid derivatives. In one aspect, the present invention provides a process for producing a diammonium salt.

Production of a Diammonium Salt

An aspect of the present invention is to provide a process for producing a diammonium salt, comprising the steps of providing an unsaturated amine salt and subjecting the unsaturated amine salt to self-metathesis in the presence of a metathesis catalyst to give a diammonium salt.

Providing an Unsaturated Amine Salt

Any suitable unsaturated amine salt may be used in the process of the present invention such as in the process for producing a diammonium salt. The unsaturated amine salt may be a commercially available compound or may be synthesized specifically for the process for producing a diammonium salt. One approach to synthesizing an unsaturated amine salt is to subject an unsaturated amine compound to a standard silver chloride salt elimination reaction. Other methods of synthesizing unsaturated amine salts from the corresponding amines are well known in the art.

One example of a suitable unsaturated amine salt is a compound of Formula I

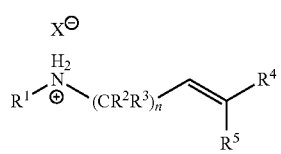

Formula I wherein each $R^1$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

each $R^2$ and $R^3$ are each independently selected from the group consisting of H, optionally substituted $C_1$-$C_{12}$alkyl, C(=O)$R^6$, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

$R^4$ and $R^5$ are each independently selected from the group consisting of H, optionally substituted $C_1$-$C_{20}$alkyl, $(CR^2R^3)_n NH_2^+ R^1$, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

each n is an integer independently selected from the group consisting of 1, 2, 3, 4, 5, 6, 7, 8, 9, 10, 11, 12, 13, 14, 15, 16, 17, 18, 19 and 20;

$X^-$ is a counterion;

$R^6$ is $NR^{6a}R^{6b}$; and $R^{6a}$ and $R^{6b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino.

In one embodiment, $R^1$ is selected from the group consisting of H and optionally substituted $C_1$-$C_{12}$alkyl. In another embodiment, $R^1$ is selected from the group consisting of H and $C_1$-$C_8$alkyl. In a further embodiment, $R^1$ is selected from the group consisting of H and $C_1$-$C_6$alkyl. In still a further embodiment, $R^1$ is H.

In one embodiment, $R^2$ is selected from the group consisting of H, optionally substituted $C_1$-$C_{12}$alkyl and $C(=O)R^6$. In another embodiment, $R^2$ is selected from the group consisting of H, $C_1$-$C_{12}$alkyl and $C(=O)R^6$. In a further embodiment, $R^2$ is selected from the group consisting of H, $C_1$-$C_6$alkyl and $C(=O)R^6$. In still a further embodiment, $R^2$ is H.

In one embodiment, $R^3$ is selected from the group consisting of H, optionally substituted $C_1$-$C_{12}$alkyl and $C(=O)R^6$. In another embodiment, $R^3$ is selected from the group consisting of H, $C_1$-$C_{12}$alkyl and $C(=O)R^6$. In a further embodiment, $R^3$ is selected from the group consisting of H, $C_1$-$C_6$alkyl and $C(=O)R^6$. In still a further embodiment, $R^3$ is H.

In one embodiment n is an integer selected from the group consisting of 1, 2, 3, 4, 5, 6, 7, 8, 9 and 10. In another embodiment n is an integer selected from the group consisting of 1, 2, 3, 4 and 5. In a further embodiment n is an integer selected from the group consisting of 1, 2 and 3. In still a further embodiment, n is 1. In another embodiment, n is 2. In still another embodiment, n is 3.

In one embodiment $R^4$ is selected from the group consisting of H, optionally substituted $C_1$-$C_{20}$alkyl and $(CR^2R^3)_n NH_2^+ R^1$. In another embodiment $R^4$ is selected from the group consisting of H, $C_1$-$C_{20}$alkyl and $(CR^2R^3)_n NH_2^+ R^1$. In still another embodiment $R^4$ is H. In another embodiment, $R^4$ is $(CR^2R^3)_n NH_2^+ R^1$.

In one embodiment $R^5$ is selected from the group consisting of H, optionally substituted $C_1$— and $(CR^2R^3)_n NH_2^+ R^1$. In another embodiment $R^5$ is selected from the group consisting of H, $C_1$-$C_{20}$alkyl and $(CR^2R^3)_n NH_2^+ R^1$. In still another embodiment $R^5$ is H. In another embodiment, $R^5$ is $(CR^2R^3)_n NH_2^+ R^1$.

The counterion $X^-$ can be any suitable counterion. The counterion can be used to tune the solubility and reactivity of the compound of Formula I. Therefore particular counterions can be selected so as to produce a desired solubility and reactivity. Once the basic form of the compound of Formula I has been chosen a skilled addressee can usually readily determine a mutual counterion to provide the desired solubility properties. Examples of suitable counterions include $BF_4^-$, $TsO^-$, $Cl^-$, $TfO^-$, $TFA^-$, $Adipate^{2-}$, $BSA^-$, $MsO^-$, $HSO_4^-$, $F^-$, $Br^-$, $I^-$, $H_2AsO_4^-$, $H_2PO_4^-$, $H_2AsO_3^-$, $HPO_4^{2-}$, $H_2PO_4^-$, $SO_4^{2-}$, $NO_3^-$, $NO_2^-$, $S_2O_3^{2-}$, $HSO_3^-$, $ClO_4^-$, $IO_3^-$, $ClO_3^-$, $BrO_3^-$, $ClO_2^-$, $CrO_4^{2-}$, $HCO_3^-$, $Cr_2O_7^{2-}$, $ClCH_2COO^-$, $HCOO^-$, $OCN^-$, $HC_2O_4^-$, $B(OR)_4^-$, $B(OH)_4^-$, $CF_2HSO_2$—$O^-$, $CFH_2SO_2$—$O^-$ and alkyl aryl sulfonates. In one embodiment, $X^-$ is selected from the group consisting of $TsO^-$, $BF_4^-$ and $TfO^-$. In one embodiment, $X^-$ is $TsO^-$. In another embodiment, $X^-$ is $TfO^-$.

Specific compounds of Formula I that may be used in the self-metathesis reaction include the following:

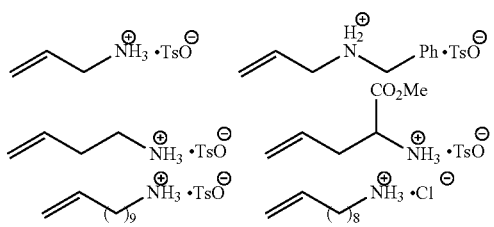

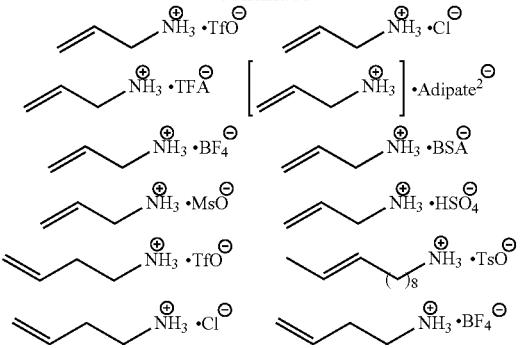

Subjecting the Unsaturated Amine Salt to Self-Metathesis

The unsaturated amine salt is subjected to self-metathesis in the presence of a metathesis catalyst to give a diammonium salt. This reaction can be carried out in any suitable solvent that does not interfere with the reaction. The solvent that is chosen will largely depend upon the properties of the unsaturated amine salt and its solubility. In one embodiment the self-metathesis reaction is performed in a solvent in which the unsaturated amine salt is more soluble than the diammonium salt. If the diammonium salt is less soluble than the unsaturated amine salt, the likelihood of the diammonium salt undergoing side reactions is reduced. Examples of solvents that can be used in the self-metathesis reaction include pentane, cyclopentane, hexane, 1-chlorobutane, 1,2-dichloroethane, n-butyl acetate, methyl tert-butyl ether, cyclohexane, benzene, toluene, dioxane, chloroform, diethyl ether, THF, EtOAc, acetone, DMF and $CH_2Cl_2$, xylene and mixtures thereof. In one embodiment, the solvent is selected from the group consisting of EtOAc, $CH_2Cl_2$ and mixtures thereof. In another embodiment, the solvent is $CH_2Cl_2$. In a further embodiment, the solvent is EtOAc.

The self-metathesis reaction can be carried out at any suitable temperature. Typically, the reaction will be performed at between 0 degrees Celsius and 100 degrees Celsius. In one embodiment, the reaction is performed at greater than 20 degrees Celsius. In a further embodiment, the reaction is performed under reflux. Another approach is to perform the self-metathesis under microwave irradiation.

The self-metathesis reaction is performed in the presence of a metathesis catalyst. Any suitable catalyst that allows self-metathesis to occur can be used. In one embodiment the catalysts is a metal complex. In one embodiment the metal in the metal complex is selected from the group consisting of ruthenium, molybdenum and tungsten. In one embodiment the catalyst is a Ruthenium-alkylidene catalyst. Examples of suitable catalysts include Schrock catalysts and Grubbs' catalysts and later generation analogues thereof. In one embodiment, the catalyst is a Hoveyda Grubbs catalyst. In a further embodiment, the catalyst is a first or second generation Grubbs' catalyst. In still a further embodiment the catalyst is a first generation Hoveyda Grubbs catalyst. In another embodiment the catalyst is a second generation Hoveyda Grubbs catalyst. The amount of catalyst will vary although a typical amount of catalyst to be used is from 1 to 20 mol %. In one embodiment the amount of catalyst to be used is from 1 to 10 mol %. In a further embodiment the amount of catalyst to be used is 5 mol %.

Specific diammonium salts that may be produced from the self-metathesis reaction include the following:

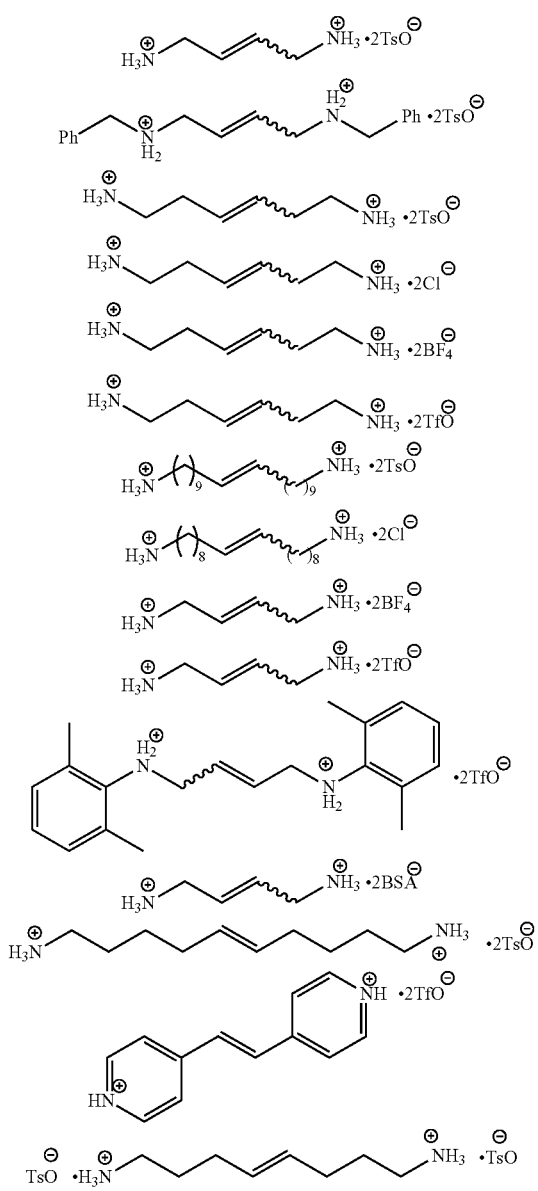

The hydrogenation may be performed at any suitable temperature. In one embodiment, the hydrogenation is performed at a temperature ranging from 0 degrees Celsius to 100 degrees Celsius. In another embodiment, the hydrogenation is performed at a temperature ranging from 20 degrees Celsius to 80 degrees Celsius. In a further embodiment the hydrogenation is performed at 60 degrees Celsius. In still a further embodiment the hydrogenation is performed in standard laboratory conditions.

In one embodiment, the self-metathesis step and the hydrogenating step are performed in series, without isolation of the diammonium salt (or after filtration of the salt) after self-metathesis. Typically the self-metathesis reaction will be performed and the reaction mixture concentrated, such as via evaporation. The concentrated reaction mixture can then be diluted by addition of a further solvent for the hydrogenating step. Typically the further solvent will be a protic solvent, such as butanol, isopropanol, propanol, ethanol, methanol, acetic acid and water. In one embodiment the further solvent is methanol.

In one embodiment the metathesis catalyst can also be used as the hydrogenation catalyst. For example the Hoveyda Grubbs second generation catalyst can be used as a hydrogenation catalyst. One advantage of this approach is that the hydrogenating step can be performed at relatively low pressures and without the use of strong base additives.

Specific saturated diammonium salts that can be produced from the hydrogenation reaction include the following:

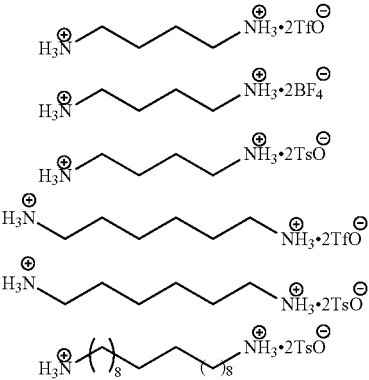

Production of an Amino Acid Salt or Derivative Thereof

Another aspect of the invention is to provide a process for producing an amino acid salt or derivative thereof comprising the steps of providing an unsaturated amine salt and subjecting the unsaturated amine salt to cross-metathesis with a compound of Formula II Hydrogenating the Diammonium Salt The diammonium salt formed from self-metathesis can be hydrogenated to give a saturated diammonium salt. Diammonium compounds, especially saturated diammonium compounds once converted to the free base, have many commercial applications. For example, the diamino compound 1,6-diaminohexane is a monomer that is used to synthesize Polyamide 66, also known as Nylon66 and is a fully saturated moiety.

Any reaction conditions that are suitable for hydrogenation to occur can be used in the conversion of this type. In one embodiment, a hydrogen source for the hydrogenation reaction is hydrogen gas. In a further embodiment, the hydrogenation is performed at a hydrogen pressure of 0 to 200 psi. In another embodiment the hydrogenation is performed at 60 to 120 psi. In still another embodiment the hydrogenation is performed at 90 psi. In a further embodiment the hydrogenation is performed at 0 to 90 psi. In still a further embodiment the hydrogenation is performed at 50 to 70 psi. In another embodiment the hydrogenation is performed at 60 psi.

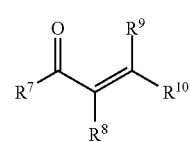

Formula II wherein $R^7$ is selected from the group consisting of OH, $OR^{7a}$ and $NR^{7a}R^{7b}$;

$R^8$ is selected from the group consisting of H and $C_1$-$C_{12}$alkyl;

$R^9$ and $R^{10}$ are each independently selected from the group consisting of H, $C_1$-$C_{12}$alkyl, $C_2$-$C_{12}$alkenyl, $C_2$-$C_{12}$alkynyl and C(=O)$R^7$; and $R^{7a}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

in the presence of a metathesis catalyst to give the amino acid salt or derivative thereof.

Providing an Unsaturated Amine Salt

Any suitable unsaturated amine salt may be used in the process for producing an amino acid. The unsaturated amine salt may be a commercially available compound or may be synthesized specifically for the process for producing an amino acid. In one embodiment the unsaturated amine salt is produced by a silver chloride salt elimination reaction with a primary amine. Other methods of synthesizing unsaturated amine salts from the corresponding amines are well known in the art.

One example of a suitable unsaturated amine salt is a compound of Formula I as described previously.

Subjecting the Unsaturated Amine Salt to Cross-Metathesis with a Compound of Formula II The unsaturated amine salt is subjected to cross-metathesis with a compound of Formula II

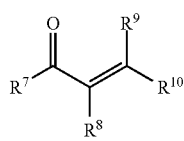

Formula II wherein $R^7$ is selected from the group consisting of OH, O$R^{7a}$ and N$R^{7a}R^{7b}$;

$R^8$ is selected from the group consisting of H and $C_1$-$C_{12}$alkyl;

$R^9$ and $R^{10}$ are each independently selected from the group consisting of H, $C_1$-$C_{12}$alkyl, $C_2$-$C_{12}$alkenyl, $C_2$-$C_{12}$alkynyl and C(=O)$R^7$; and $R^{7a}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;

in the presence of a metathesis catalyst to give an amino acid or derivative thereof.

In one embodiment $R^7$ is selected from the group consisting of OH and O$C_1$-$C_6$alkyl. In another embodiment $R^7$ is OH. In still another embodiment, $R^7$ is O$C_4$alkyl.

In one embodiment $R^8$ is selected from the group consisting of H and $C_1$-$C_6$alkyl. In another embodiment $R^8$ is H.

In one embodiment $R^9$ is selected from the group consisting of H and $C_1$-$C_6$alkyl. In another embodiment $R^9$ is H.

In one embodiment $R^{10}$ is selected from the group consisting of H and $C_1$-$C_6$alkyl. In another embodiment $R^{10}$ is H.

In one embodiment, the compound of Formula II is a compound of Formula III

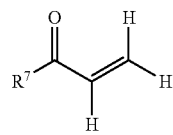

Formula III wherein $R^7$ is selected from the group consisting of OH, O$R^{7a}$ and N$R^{7a}R^{7b}$; and $R^{7a}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino.

In still another embodiment, $R^7$ is selected from the group consisting of OH and O$C_4$alkyl.

Specific compounds of Formula II include the following:

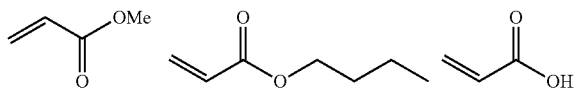

The cross-metathesis reaction can be carried out in any suitable solvent, where the solvent that is chosen may depend upon the properties of the unsaturated amine salt to be used. In one embodiment the cross-metathesis reaction is performed in a solvent in which the unsaturated amine salt has an appropriate solubility which minimises side reactions (i.e. isomerisation) but promotes reaction with a compound of Formula (II). Suitable solvents include the solvents previously discussed for the self-metathesis reaction of an unsaturated amine salt.

The cross-metathesis reaction can be carried out at any suitable temperature. Suitable temperatures include those previously discussed for the self-metathesis reaction of an unsaturated amine salt.

The cross-metathesis reaction is performed in the presence of a metathesis catalyst. Any suitable catalyst that allows cross-metathesis to occur can be used. Suitable catalysts include the catalysts previously discussed for the self-metathesis reaction of an unsaturated amine salt.

In theory the reaction can be carried out across a wide range of reaction stoichiometry with the amount of compound of formula (II) being from as little as 0.1 mol equivalent per 1 mol equivalent of the unsaturated amine salt to as much as 30 mole equivalent per 1 mole equivalent of the unsaturated amine salt.

Nevertheless, it should also be noted that the unsaturated amine salt can also undergo self-metathesis as well as cross-metathesis as discussed previously. As such it is advantageous to control the reaction stoichiometry in order to obtain the desired reaction product. Accordingly, it is preferred that the compound of Formula II is present in excess so that the cross-metathesis reaction is favoured over self-metathesis. For example, 1 mol equivalent of an unsaturated amine salt can be reacted with a compound of Formula II that is present in an amount ranging from 1.5 to 100 mol equivalents. In one embodiment, the amount of the compound of Formula II ranges from 2 to 20 mol equivalents for 1 mol equivalent of the unsaturated amine salt. In another embodiment the amount of the compound of Formula II ranges from 2 to 10 mol equivalents for 1 mol equivalent of the unsaturated amine salt. In a further embodiment the amount of the compound of Formula II is 2 mol equivalents for 1 mol equivalent of the unsaturated amine salt. In still a further embodiment the amount of the compound of Formula II is 10 mol equivalents for 1 mol equivalent of the unsaturated amine salt.

Specific amino acid salts or derivatives thereof that may be produced from the cross-metathesis reaction include the following:

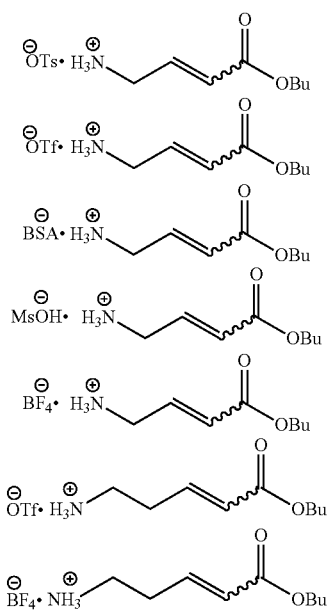

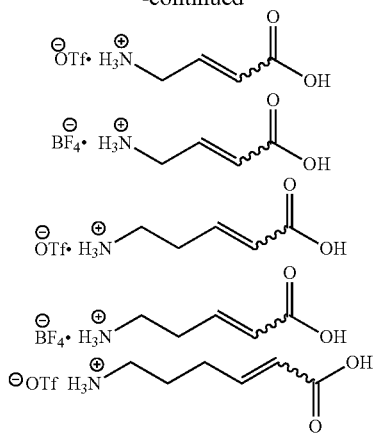

Hydrogenating the Amino Acid

The amino acid salt or derivative thereof formed from cross-metathesis can be hydrogenated to give a saturated amino acid salt or derivative thereof. Any reaction conditions that are suitable for hydrogenation to occur can be used. In one embodiment, the hydrogen source is hydrogen gas. Suitable hydrogen pressures include the hydrogen pressures previously discussed for the hydrogenation of a diammonium salt.

The hydrogenation may be performed at any suitable temperature. Suitable temperatures include the temperatures previously discussed for the hydrogenation of a diammonium salt.

In one embodiment, the cross-metathesis step and the hydrogenating step are performed in series, without isolation of the amino acid salt or derivative thereof after cross-metathesis. Typically the cross-metathesis reaction will be performed and the reaction mixture concentrated, such as via evaporation. The concentrated reaction mixture can then be diluted by addition of a further solvent for the hydrogenating step. Typically the further solvent will be a protic solvent as previously discussed for the hydrogenation of a diammonium salt.

In one embodiment the metathesis catalyst can also be used as the hydrogenation catalyst. For example the Hoveyda Grubbs second generation catalyst can be used as a hydrogenation catalyst. One advantage of this approach is that the hydrogenating step can be performed at relatively low pressures and without the use of strong base additives.

Specific saturated amino acid salts or derivatives thereof that may be produced from the hydrogenation reaction include the following:

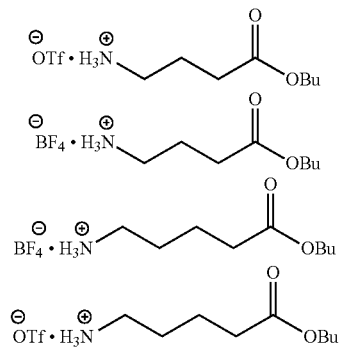

-continued

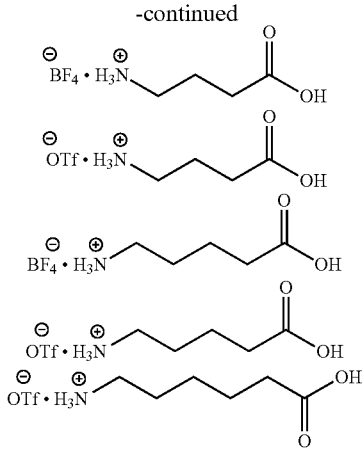

In particular, the amino acid

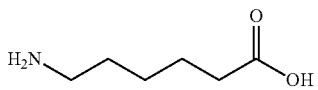

can be used as a monomer for the synthesis of the commercially important polymer Polyamide 66, also known as Nylon6. This monomer can therefore replace caprolactam, which Nylon6 is typically synthesized from. As the synthesis of caprolactam produces 5 kg of ammonium sulfate for every 1 kg of monomer, it is desirable to substitute other monomers for caprolactam where possible.

One advantage of the processes of the invention is that they can employ non-toxic commercially available feedstocks. Current industrial methods mostly rely on feedstocks supplied from the exhausting petrochemical industry. They utilize harmful chemicals (such as cyanide or acrylonitrile) and dangerous high pressure and/or temperature reaction conditions. These harsh methods only tolerate simple chemical functionality, which sets limitations on the chain length of the monomers and the ability to fine tune the monomer/polymer properties.

The invention will now be described with reference to the following examples.

EXAMPLES

The symbols, abbreviations and conventions in the processes, schemes, and examples are consistent with those used in the contemporary scientific literature. Specifically but not meant as limiting, the following abbreviations may be used in the examples and throughout the specification.

g (grams)
L (liters)
mol (moles)
MeOH (methanol)
EtOAc (ethyl acetate)
mg (milligrams)
mL (milliliters)
psi (pounds per square inch)
mmol (millimoles)
h (hours)

Unless otherwise indicated, all temperatures are expressed in ° C. (degree Celsius). All reactions are conducted at standard laboratory conditions unless otherwise mentioned.

All reagents were purchased from Aldrich and used without further purification unless specified. Anhydrous p-toluenesulphonic acid and benzenesulphonic acid were dried under vacuum (1 mmHg) at 100-110° C. for 4 h. All solvents were purchased from Merck and used without further purification unless specified. Dichloromethane was dried over CaCl$_2$, distilled from CaH and deoxygenated by applying a nitrogen sparge prior to use in all metathesis reactions. Ethyl acetate was deoxygenated by applying a nitrogen sparge prior to use in all metathesis reactions.

Example 1

General Procedure for the Self-Metathesis of an Unsaturated Amine Salt

Under an inert atmosphere of nitrogen, a Schlenk tube was charged with an unsaturated amine salt (0.15-0.16 mmol), second generation Hoveyda Grubbs catalyst (5 mol %) and a small magnetic stir bar. CH$_2$Cl$_2$ (2-4 mL) or EtOAc (2-4 mL) was added through a rubber septum and the tube was sealed and heated at reflux under nitrogen for between 16 and 24 hours. The vessel was then cooled to standard laboratory conditions and the reaction solvent was removed by rotary evaporation. The resulting mixture was dissolved in a minimum volume of acetone (or dichloromethane) and triturated with excess diethyl ether (or hexane, or acetone) (approx 1:10). Filtration (or centrifugation) gave the diammonium salt.

Compounds that were produced using this process include the following:

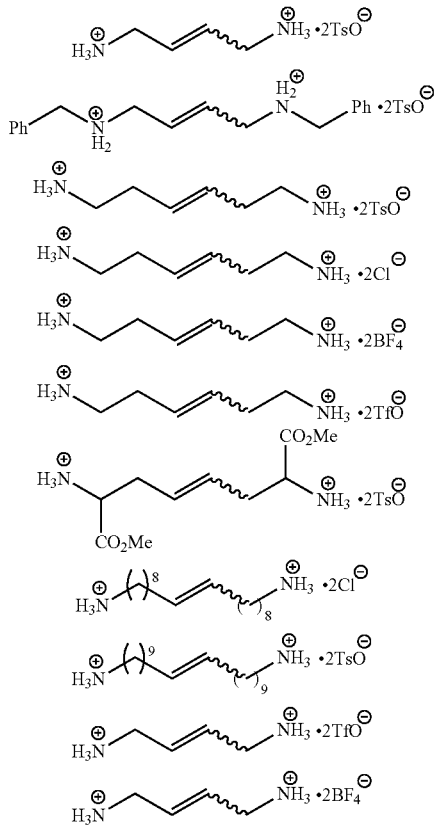

-continued

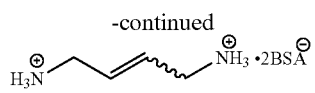

Exemplary yields include the following:

| Compound | Yield % |
| --- | --- |
| H$_3$N$^⊕$~~~NH$_3$·2TsO$^⊖$ | 40 |
| Ph~N$^⊕$H$_2$~~~N$^⊕$H$_2$~Ph·2TsO$^⊖$ | 23 |
| H$_3$N$^⊕$~~~~NH$_3$·2TsO$^⊖$ | 92 |
| H$_3$N$^⊕$~~~~NH$_3$·2Cl$^⊖$ | 38 |
| H$_3$N$^⊕$~~~~NH$_3$·2BF$_4$$^⊖$ | 91 |
| H$_3$N$^⊕$~~~~NH$_3$·2TfO$^⊖$ | 83 |
| H$_3$N$^⊕$~($)_8$~~~($)_8$NH$_3$·2Cl$^⊖$ | 81 |
| H$_3$N$^⊕$~($)_9$~~~($)_9$NH$_3$·2TsO$^⊖$ | 92 |
| H$_3$N$^⊕$~~~NH$_3$·2TfO$^⊖$ | 91 |
| H$_3$N$^⊕$~~~NH$_3$·2BF$_4$$^⊖$ | Quant |
| H$_3$N$^⊕$~~~NH$_3$·2BSA$^⊖$ | 25 |

Example 2

General Procedure for the Self-Metathesis of an Unsaturated Amine Salt Under Microwave Irradiation Under an inert atmosphere of nitrogen, a quartz microwave vessel was charged with an unsaturated amine salt (0.22 mmol), second generation Hoveyda Grubbs catalyst (5 mol %), CH$_2$Cl$_2$ (2 mL) and a small magnetic stir bar. The vessel was sealed and irradiated in a CEM discovery microwave (Benchmate) at 100° C., 100 watts for 2 h with cooling. The vessel was then cooled to standard laboratory conditions and the solvent removed by rotary evaporation. The resulting mixture was dissolved in a minimum volume of acetone (or dichloromethane) and triturated with excess diethyl ether (or hexane, or acetone) (approx 1:10). Filtration (or centrifugation) gave the diammonium salt.

Compounds that were produced using this process include the following:

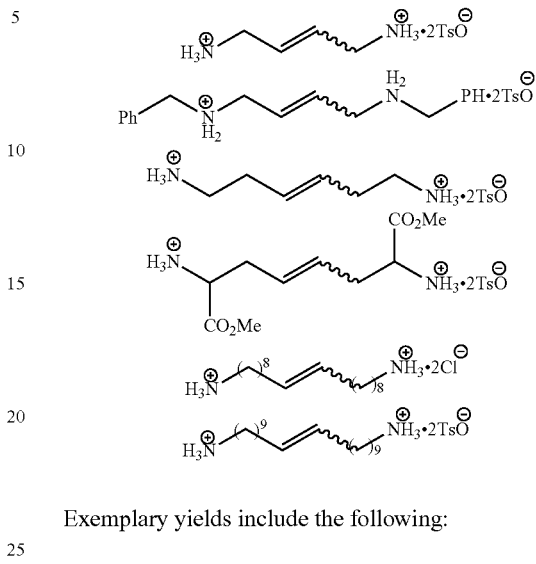

Exemplary yields include the following:

| Compound | Microwave Yield % |
| --- | --- |
| H$_3$N$^⊕$~~~NH$_3$·2TsO$^⊖$ | 74 |
| Ph~N$^⊕$H$_2$~~~N$^⊕$H$_2$~Ph·2TsO$^⊖$ | 46 |
| H$_3$N$^⊕$~~~~NH$_3$·2TsO$^⊖$ | 95 |
| H$_3$N$^⊕$~($)_8$~~~($)_8$NH$_3$·2Cl$^⊖$ | 82 |
| H$_3$N$^⊕$~($)_9$~~~($)_9$NH$_3$·2TsO$^⊖$ | 88 |

Example 3

General Procedure for the Self-Metathesis of an Unsaturated Amine Salt Followed by Hydrogenation of the Resulting Diammonium Salt Under an inert atmosphere of nitrogen, a Schlenk tube was charged with an unsaturated amine salt (0.15-0.16 mmol), second generation Hoveyda Grubbs catalyst (5 mol %) and a small magnetic stir bar. CH$_2$Cl$_2$ (2-4 mL) or EtOAc (2-4 mL) was added through a rubber septum and the tube was sealed and heated at reflux under nitrogen for between 16 and 24 hours. The crude reaction mixture was then exposed to air and concentrated in vacuo, re-dissolved in methanol (2 mL) and transferred to a Fischer-Porter pressure tube. The tube was evacuated with hydrogen, charged to a final pressure of 0-60 psi and left to stir at ambient temperature overnight. The vessel was then vented to air and the solvent was removed by rotary evaporation. The resulting mixture was dissolved in a minimum volume of acetone (or dichloromethane) and triturated with excess diethyl ether (or hexane, or acetone) (approx 1:10). Filtration (or centrifugation) gave the saturated diammonium salt.

Compounds that were produced using this process include the following:

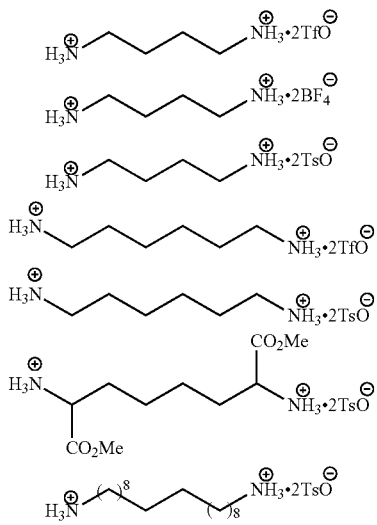

Exemplary yields include the following:

| Compound | Yield % |
|---|---|
| H₃N⊕~~~~NH₃·2TfO⊖ | 90 |
| H₃N⊕~~~~NH₃·2BF₄⊖ | >95 |
| H₃N⊕~~~~NH₃·2TsO⊖ | 57 |
| H₃N⊕~~~~~NH₃·2TfO⊖ | 61 |
| H₃N⊕~~~~~NH₃·2TsO⊖ | >95 |
| H₃N⊕(~)₈(~)₈NH₃·2TsO⊖ | >95 |

Example 4

General Procedure for the Cross-Metathesis of an Unsaturated Amine Salt with Butyl Acrylate or Methyl Acrylate Under an inert atmosphere of nitrogen, a Schlenk tube was charged with an unsaturated amine salt (1 equivalent), butyl acrylate or methyl acrylate (1-10 equivalents), second generation Hoveyda Grubbs catalyst (5 mol %) and a small magnetic stir bar. CH₂Cl₂ (2-4 mL) or EtOAc (2-4 mL) was added through a rubber septum and the tube was sealed and heated at reflux for between 2 and 24 hours, optionally under nitrogen. The vessel was then cooled to standard laboratory conditions and the reaction mixture was transferred to a separating funnel. The organic layer was extracted with water (3×10 mL). The combined extract was optionally extracted further with ethyl acetate before being concentrated. The combined aqueous extract was concentrated in vacuo to give the amino acid salt in high purity. The residue was then optionally extracted with ether (3×10 mL) to remove an insoluble precipitate. The combined organic extract was concentrated in vacuo to give the amino acid salt.

Compounds that were produced using this process include the following:

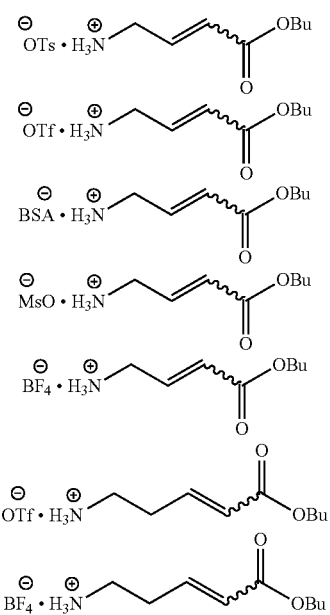

Exemplary conversions include the following:

| Compound | NMR Yield % |
|---|---|
| OTs·H₃N⊕~~~CO₂Bu | 12 |
| OTf·H₃N⊕~~~CO₂Bu | 72 |
| BSA·H₃N⊕~~~CO₂Bu | 13 |
| MsO·H₃N⊕~~~CO₂Bu | 2 |
| BF₄·H₃N⊕~~~CO₂Bu | >95 |

25
-continued

| Compound | NMR Yield % |
|---|---|
| OTf·H₃N⁺ ~~~ C(O)OBu | >95 |
| BF₄·H₃N⁺ ~~~ C(O)OBu | >95 |
| ⁻OTs  H₃N⁺ ~~~ C(O)OMe | 26% |
| ⁻OBF₄  H₃N⁺ ~~~ C(O)OMe | 84% |
| ⁻OTf  H₃N⁺ ~~~ C(O)OMe | >99% |

Example 5

General Procedure for the Cross-Metathesis of an Unsaturated Amine Salt with Acrylic Acid Under an inert atmosphere of nitrogen, a Schlenk tube was charged with an unsaturated amine salt (1 equivalent), acrylic acid (1-20 equivalents), second generation Hoveyda Grubbs catalyst (5 mol %) and a small magnetic stir bar. CH₂Cl₂ (2-4 mL) or EtOAc (2-4 mL) was added through a rubber septum and the tube was sealed and heated at reflux for between 2 and 24 hours, optionally under nitrogen. The vessel was then cooled to standard laboratory conditions and the reaction mixture was transferred to a separating funnel. The organic layer was extracted with water (3×10 mL). The combined organic extract was optionally extracted further with ethyl acetate before being concentrated. The combined aqueous extract was concentrated in vacuo to give the amino acid salt in high purity. The residue was then optionally extracted with ether (3×10 mL). The combined organic extract was concentrated in vacuo to give the amino acid salt.

Compounds that were produced using this process include the following:

26

Exemplary conversions include the following:

| Compound | NMR Yield % |
|---|---|
| OTf·H₃N⁺ ~~~ C(O)OH | 70% |
| BF₄·H₃N⁺ ~~~ C(O)OH | 70% |
| BF₄·H₃N⁺ ~~~ C(O)OH | >95% |
| OTf·H₃N⁺ ~~~ C(O)OH | >95% |

Example 6

Cross Metathesis and Hydrogenation Reactions Performed in Series

Under an inert atmosphere of nitrogen, a Schlenk tube was charged with an unsaturated amine salt (1 equivalent), acrylic acid or acrylate ester (1-20 equivalents), second generation Hoveyda Grubbs catalyst (5 mol %) and a small magnetic stir bar. CH₂Cl₂ (2-4 mL) or EtOAc (2-4 mL) was added through a rubber septum and the tube was sealed and heated at reflux for between 2 and 24 hours, optionally under nitrogen. The crude reaction mixture was then exposed to air and concentrated in vacuo, re-dissolved in methanol (1-4 mL) and transferred to a Fischer-Porter pressure tube. The tube was evacuated with hydrogen, charged to a final pressure of 90 psi and left to stir at 60° C. overnight. The vessel was then vented to air and the solvent was removed by rotary evaporation. The organic layer was extracted with water (3×10 mL). The combined aqueous extract was concentrated in vacuo to give the amino acid salt in high purity. The residue was then optionally extracted with ether (3×10 mL). The combined organic extract was concentrated in vacuo to give the amino acid salt.

Exemplary compounds generated using this process include the following:

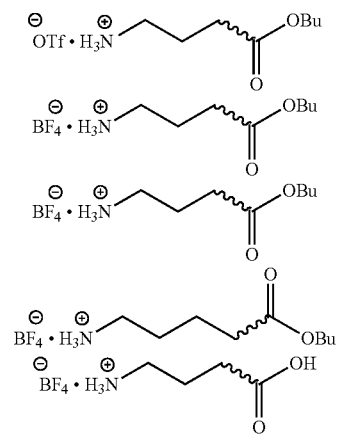

-continued

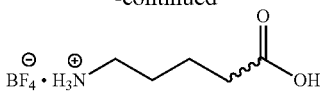

Exemplary conversions include the following:

| Compound | NMR Yield % |
|---|---|
| 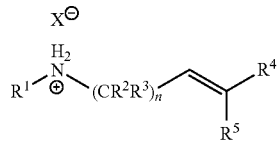 | >95% |
| | >95% |
| | >95% |
| | >95% |
| | >95% |
| | >95% |

The invention claimed is:

1. A process for producing an amino acid salt or derivative thereof comprising the steps of:
providing an unsaturated amine salt or derivative thereof; and
wherein the unsaturated amine salt is a compound of Formula I Formula I

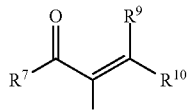

wherein
each $R^1$ is independently selected from the group consisting of H, optionally $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;
$R^2$ and $R^3$ are each independently selected from the group consisting of H and $C_1$-$C_{12}$alkyl;
$R^4$ and $R^5$ are each independently selected from the group consisting of H, and $C_1$-$C_{20}$alkyl,
n is an integer selected from the group consisting of 1, 2, 3, 4, 5, 6, 7, 8, 9, 10, 11, 12, 13, 14, 15, 16, 17, 18, 19 and 20;
$X^-$ is a counterion; and
subjecting the unsaturated amine salt to
cross-metathesis with a compound of Formula II Formula II wherein
$R^7$ is selected from the group consisting of OH, $OR^{7a}$ and $NR^{7a}R^{7b}$;
$R^8$ is selected from the group consisting of H and $C_1$-$C_{12}$alkyl;
$R^9$ and $R^{10}$ are each independently selected from the group consisting of H, $C_1$-$C_{12}$alkyl, $C_2$-$C_{12}$alkenyl, $C_2$-$C_{12}$alkynyl and $C(=O)R^7$; and
$R^{7}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino;
in the presence of a metathesis catalyst to give the amino acid salt or derivative thereof.

2. The process according to claim 1, wherein $R^1$ is H, $R^2$ is H and $R^3$ is H.

3. The process according to claim 1, wherein n is selected from the group consisting of 1, 2, 3, 4, 5, 6, 7, 8, 9, and 10.

4. The process according to claim 1, wherein $R^4$ is H and $R^5$ is H.

5. The process according to claim 1, wherein $X^-$ is selected from the group consisting of $BF_4^-$, $TsO^-$, $Cl^-$, $TfO^-$, $TFA^-$, Adipate$^{2-}$, $BSA^-$, $MsO^-$, $HSO_4^-$, $F^-$, $Br^-$, $I^-$, $H_2AsO_4^-$, $H_2PO_4^-$, $H_2AsO_3^-$, $HPO_4^{2-}$, $H_2PO_4^-$, $SO_4^{2-}$, $NO_3^-$, $NO_2^-$, $S_2O_3^{2-}$, $HSO_3^-$, $ClO_4^-$, $IO_3^-$, $ClO_3^-$, $BrO_3^-$, $ClO_2^-$, $CrO_4^{2-}$, $HCO_3^-$, $Cr_2O_7^{2-}$, $ClCH_2COO^-$, $HCOO^-$, $OCN^-$, $HC_2O_4^-$, $B(OR)_4^-$, $B(OH)_4^-$, $CF_2HSO_2$—$O^-$, $CFH_2SO_2$—$O^-$ and alkyl aryl sulfonates.

6. The process according to claim 5, wherein $X^-$ is selected from the group consisting of $BF_4^-$, $TsO^-$ and $TfO^-$.

7. The process according to claim 1, wherein $R^7$ is selected from the group consisting of OH and $OC_1$-$C_6$alkyl.

8. The process according to claim 1, wherein $R^8$ is H, $R^9$ is H and $R^{10}$ is H.

9. The process according to claim 1, wherein the compound of Formula II is a compound of Formula III

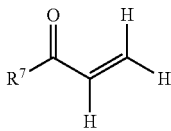

Formula III wherein $R^7$ is selected from the group consisting of OH, $OR^{7a}$ and $NR^{7a}R^{7b}$; and $R^{7a}$ and $R^{7b}$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy and optionally substituted $C_1$-$C_{12}$alkylamino.

10. A process according to claim 1, wherein the catalyst is a metal complex wherein the metal in the metal complex is selected from the group consisting of ruthenium, molybdenum and tungsten.

11. A process according to claim 1, wherein the catalyst is a ruthenium-alkylidene catalyst, a Grubbs catalyst or a later generation analogue, or a Hoveyda Grubbs second generation catalyst.

12. The process according claim 1, further comprising the step of hydrogenating the amino acid salt or derivative thereof; formed from cross-metathesis to give a saturated amino acid salt.

13. The process according to claim 12, wherein the cross-metathesis step and the hydrogenating step are performed in series without isolation of the amino acid salt or derivative thereof; after cross-metathesis.

* * * * *